United States Patent [19]
Ottoboni et al.

[11] Patent Number: 5,731,005
[45] Date of Patent: Mar. 24, 1998

[54] HYDROGEL-BASED MICROSPHERE DRUG DELIVERY SYSTEMS

[75] Inventors: Thomas B. Ottoboni, Belmont; Lisa B. Jungherr, Los Altos; Ronald K. Yamamoto, San Francisco, all of Calif.

[73] Assignee: Vitaphore Corporation, Menlo Park, Calif.

[21] Appl. No.: 475,590

[22] Filed: Jun. 6, 1995

Related U.S. Application Data

[62] Division of Ser. No. 106,287, Aug. 13, 1993, abandoned.

[51] Int. Cl.[6] .................... A61K 9/16; A61K 47/42; A61K 47/32; A61K 47/36
[52] U.S. Cl. ............... 424/499; 424/501; 424/427; 514/912; 514/913; 514/914; 514/952
[58] Field of Search ................. 424/427, 499, 424/501, 484, 486–88; 514/912–14, 952

[56] References Cited

U.S. PATENT DOCUMENTS

| | | |
|---|---|---|
| 3,427,301 | 2/1969 | Needles et al. |
| 3,469,003 | 9/1969 | Haver-Lockart. |
| 3,914,402 | 10/1975 | Shell. |
| 4,001,388 | 1/1977 | Shell. |
| 4,061,787 | 12/1977 | Higgens. |
| 4,115,544 | 9/1978 | Shell. |
| 4,138,383 | 2/1979 | Rembaum et al. ............... 260/29.7 H |
| 4,140,537 | 2/1979 | Luck et al. |
| 4,221,778 | 9/1980 | Raghunathan. |
| 4,233,360 | 11/1980 | Luck et al. |
| 4,280,954 | 7/1981 | Yannas et al. |
| 4,294,241 | 10/1981 | Miyata. |
| 4,404,033 | 9/1983 | Steffan et al. |
| 4,448,718 | 5/1984 | Yannas et al. |
| 4,500,453 | 2/1985 | Shank. |
| 4,582,640 | 4/1986 | Smestad et al. |
| 4,590,020 | 5/1986 | Itaba et al. |
| 4,597,762 | 7/1986 | Walter et al. |
| 4,703,108 | 10/1987 | Silver et al. |
| 4,808,399 | 2/1989 | Rypacek et al. |
| 4,824,620 | 4/1989 | Casa et al. |
| 4,863,647 | 9/1989 | Baylor et al. |
| 4,865,846 | 9/1989 | Kaufman. |
| 4,882,150 | 11/1989 | Kaufman. |
| 4,892,700 | 1/1990 | Guerra et al. |
| 4,911,920 | 3/1990 | Jani et al. |
| 4,923,699 | 5/1990 | Kaufman. |
| 4,923,700 | 5/1990 | Kaufman ................ 424/427 |
| 4,948,540 | 8/1990 | Nigam. |
| 4,958,008 | 9/1990 | Petite et al. |
| 4,969,912 | 11/1990 | Kelman et al. |
| 4,970,298 | 11/1990 | Silver et al. |
| 4,971,954 | 11/1990 | Brodsky et al. |
| 4,981,912 | 1/1991 | Kaisha. |
| 4,996,047 | 2/1991 | Keller. |
| 5,024,742 | 6/1991 | Nesburn et al. |
| 5,041,292 | 8/1991 | Feijen. |
| 5,093,126 | 3/1992 | Jani et al. |
| 5,192,535 | 3/1993 | Davis et al. ............... 424/78.04 |

FOREIGN PATENT DOCUMENTS

| | | |
|---|---|---|
| A 0210461 | 7/1988 | European Pat. Off. |
| A 03675590 | 11/1989 | European Pat. Off. |
| 91/918644 | 11/1993 | European Pat. Off. |
| A 2 635 459 | 8/1988 | France. |
| WO 89/03207 | 4/1989 | WIPO. |
| WO-A 89/04668 | 6/1989 | WIPO. |
| WO 91/110446 | 7/1991 | WIPO. |
| WO-A 91/19481 | 12/1991 | WIPO. |
| WO 92/11038 | 7/1992 | WIPO. |
| WO 92/11871 | 7/1992 | WIPO. |

OTHER PUBLICATIONS

E. Balazs, D.B. Sweeny, A. McPherson (ed.); The Injection of Hyaluronic Acid and Reconstitued bitreous into the Vitreous Cavity; *New and Controversial Aspects of Retinal Detachment*; 36:371–376 (1968).

M. Chvapil, R. Kronenthal, W. van Winkle; Medical and Surgical Applications of Collagen; *Int. Rev. Conn. Tissues* 6:1–61 (1973).

M. Chvapil, D. Speer, W. Mora, C. Eskelson; Effect of Tanning Agent on Tissue Reaction to Tissue Implanted Collagen Sponge; *J. Surg. Res.* 35:402–409 (1983).

IN VITRO TEAR FILM MODEL

M. Dunn, T. Miyata, K. Stnzel, A. Rubin; Studies on Collagen Implants in the Vitreous; *Surgical Forum/Opthalmic Surgery* , 19:492–494 (1968).

Z. Horakova et al.; Prolongation par les Substances Col lagenes de Quelques Actions Parmacologiques; *Therapie* 22:1455–1460 (1967).

S. Richard–Blum. G. Vile; Minireview: Collagen Crosslinking; *Int. J. Biochem.* 21(11): 1185–1189.

A. Rubin, K. Stenzel; Collagen as a Biomaterial; *Technol. Rev.* 71(2):44–49 (1968).

K. Weadock, R. Olson, F. Silver; evaluation of Collagen Crosslinking Techniques; *Biomat. Med. Dev. Art. Org.* 11(4):293–318 (1983–4).

*Primary Examiner*—Edward J. Webman
*Attorney, Agent, or Firm*—Campbell & Flores LLP

[57] ABSTRACT

The present invention provides a sustained-release delivery composition for ophthalmic drugs comprising cross-linked hydrogel microspheres having a binding affinity for the drug.

8 Claims, 1 Drawing Sheet

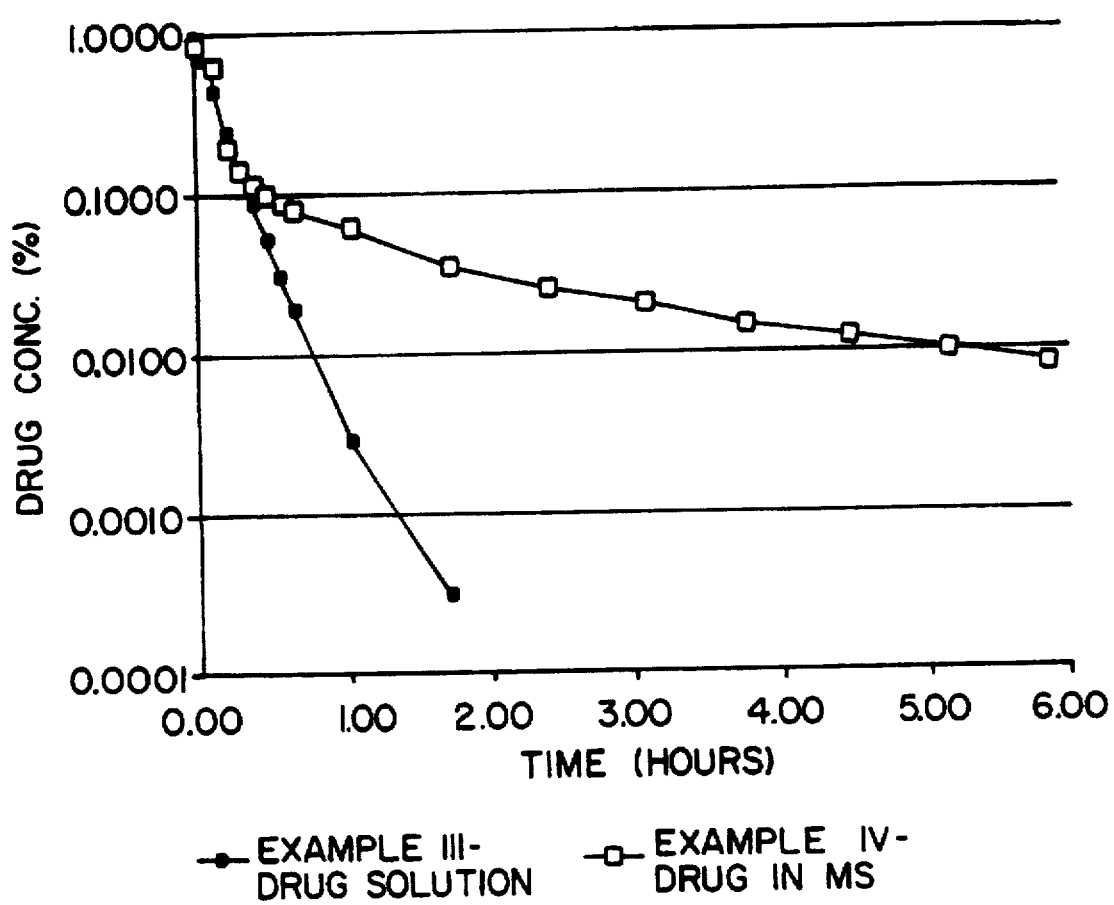

HYDROGEL-BASED MICROSPHERE DRUG DELIVERY SYSTEMS

This is a divisional application Ser. No. 08/106,287, filed Aug. 13, 1993, now abandoned.

FIELD OF THE INVENTION

The present invention is directed to drug delivery systems for the topical delivery of drugs to the ocular area using hydrogel microspheres. Hydrogels are water-swellable polymeric matrices which can absorb water to form elastic gels.

The present invention is advantageous over the following methods of topical ocular drug delivery.

Eyedrop solutions are inefficient because the solution will drain through the nasal lacrimal duct into the nasal cavity. Thus, solutions with relatively high concentrations are required, usually in the range of about 0.5 to 2% weight by volume, in order to provide an effective dose at the target site. Prolonged contact of the therapeutic agent with the eye is of course inconvenient when eyedrops must be frequently applied. In some instances due to the high dosages which are required for use of the drops there can be systemic toxic side effects. For all of the above reasons, eyedrops cannot be continuously added to the eye as a means of prolonged topical ocular delivery.

Ointments and gels as drug delivery systems may be used for prolonged delivery because of their slow dissolution. However, since they are generally very uncomfortable and blur the vision, they can only be used when the subject is inactive.

Ocular inserts such as those disclosed in U.S. Pat. Nos. 3,845,201, 4,164,559 or 4,179,497, allow prolonged delivery of a drug from the insert. However, patient compliance with proper use of the insert is low because the inserts are difficult to place in the eye, especially for elderly persons. Furthermore, retention of the insert in the eye can be a problem, and they produce an uncomfortable foreign body sensation in the eye.

Therapeutic suspensions, as opposed to eyedrop solutions, discussed above, may be used for compounds having low solubility, since the rate of release of the drug is related to its solubility in the eye. The primary application of therapeutic suspensions for the eye has been essentially limited to low-solubility steroids.

Microencapsulated drugs may be delivered to the eye, but preparation of the drug-encapsulating microspheres is complicated because the drug must be placed in the microsphere during the fabrication of the microsphere. Furthermore, normally the release of the drug from the microsphere is controlled by placing the microsphere in an aqueous system. Therefore, the microsphere can only be mixed with the delivery vehicle just prior to use, which makes its use inconvenient.

U.S. Pat. No. 4,865,846 to Kaufman discloses an ophthalmic drug delivery system in which there is a carrier in a bio-erodible material so it appears that the drug is released by bio-erosion.

The present invention is directed to an ocular delivery system comprising hydrogel microspheres which avoids the above disadvantages and which provides further advantages.

One of the advantages provided by the compositions of the present invention is that the drug can be loaded into the hydrogel microspheres after the microspheres have been formed, thus allowing for the opportunity of an intermediate sterilization step for the microspheres. Sterilization can cause side reactions and typically result in decomposition of the drug if the microspheres are sterilized when they contain the drug.

The hydrogel microspheres of the present invention also actively bind to the drug. One can load the microspheres with a concentration of drug which is higher than the concentration of the drug in the surrounding liquid carrier.

Furthermore, the hydrogel microspheres according to the present invention are essentially non-irritating to the eye because of their small particle size and soft texture.

It has also been found that the microspheres according to the present invention adhere to mucin, particularly to the proteoglycans in the mucosal surfaces. Adherence of the microspheres would also be expected on other wet, body tissues, mucosal or nonmucosal. Thus, while the microspheres can be swept out of the eye along with the normal turnover of the mucin, they will remain in the tear film for a period of time, which is sufficient to complete release of the drug.

It is critical that the particles are retained in the eye longer than is required for a majority of the drug to be delivered. The drug contained in particles that are prematurely drained from the eye is systemically delivered. Kaufman discloses that hydrogel particles less the 400 microns in their smallest dimension are rapidly drained from the eye through the punctum. While the particles of the present invention preferably have a diameter of 100 microns or less, they are effectively retained in the tear film because of their capacity to bind to ocular mucin.

Ocular mucin is primarily composed of glycoprotein, a protein backbone with covalently bound oligosaccharide side chains. The oligosaccharide chains can comprise between 50 and 80% of the weight of the mucin. Four principal forces involved in mucoadhesion are: hydrogen bonding, van der Waals, electrostatic, and hydrophobic, the strongest of these being hydrogen bonding. The macromolecules utilized in the hydrogel microspheres have functional groups capable of hydrogen bonding (e.g. carboxyl, amide, hydroxyl, amine), and it appears that the presence of these groups in the macromolecules comprising the microspheres imparts mucoadhesive character to the microspheres.

SUMMARY OF THE INVENTION

The present invention provides a sustained release delivery composition for ocular use comprising hydrogel microspheres in an aqueous carrier containing the pharmaceutically active agent with a pH and osmotic pressure acceptable to the eye. Hydrogel microspheres also contain the pharmaceutically active agent, wherein the microspheres comprise cross-linked macromolecules and macromolecules possessing an affinity for the agent such that the final delivery composition has an affinity of at least 0.8 for the agent. The cross-linked macromolecule may also be the molecule possessing the required affinity for the agent. Preferably the hydrogel microspheres will have an average diameter of not greater than about 100 microns. Furthermore, preferably at equilibrium in the composition the concentration of the active agent in the microspheres is at least twice the concentration of the agent in the carrier, due to the active binding affinity of the macromolecules within the microspheres with the agent. Methods of preparing the microspheres are also provided.

BRIEF DESCRIPTION OF THE DRAWING

In the accompanying FIGURE there is shown the drug delivery profile into a tear film model of a drug solution and of drug microspheres.

DESCRIPTION OF THE PREFERRED EMBODIMENTS

The drug delivery system according to the present invention comprises hydrogel microspheres. The microspheres are not necessarily spherical, but should have an average diameter, regardless of their shape, of preferably less than about 100 microns, and most preferably between about 5 and 50 microns, since particles of these dimensions do not irritate the eye.

The microspheres will be suspended in a carrier (pharmaceutical vehicle) suitable for contacting the eye surface and which will also contain a drug. The drug contained in the vehicle may be the same drug contained in the microspheres, may be a different drug, or may be a combination of drugs intended for delivery upon contact of the vehicle with the eye. The vehicle is aqueous, preferably a buffered solution isoosmotic with tears, such as a mannitol solution.

The composition preferably contains osmotic agents sufficient to render the composition acceptable to the eye, particularly osmotic agents which provide an osmotic pressure identical to or close to the osmotic pressure of tears. Exemplary osmotic agents are sodium chloride, lithium chloride, potassium sulfate, sodium sulfate, calcium sulfate, magnesium sulfate, mannitol, glucose, sucrose, and the like. Preservatives and antibacterial agents such as benzalkonium chloride and phenylethyl alcohol may also be utilized in the vehicle in order to provide a suitable shelf life of the composition prior to use. The preservatives and antibacterial agents are compatible with the pharmaceutically active agent, non-toxic, non-irritating to the eye and other tissues. Typical concentrations of preservatives and antibacterial agents are 0.0005% to 0.005% wt. by volume in the vehicle. Other typical optional additives include viscosity enhancers such as polyvinyl alcohol, polyethylene glycol, polyvinyl pyrrolidone, and carboxymethyl cellulose. These agents reduce the rate at which the composition leaves the eye and can enhance comfort for the user.

The drugs which may be utilized in accordance with the present invention include, but are not limited to, ophthalmic drugs, such as antibiotics such as tetracycline, neomycin, polymyxin, gramicidin, gentamicin, tobramycin, trimethoprim, choramphenicol, bacitracin, erythromycin; antibacterials such as sulfonamides, sulfacetamide, sulfamethizole and sulfisoxazole; antivirals; anti-inflammatories such as hydrocortisone, dexamethasone, fluocinolone, fluorometholone and triamcinolone; cholenergics and anticholinesterases such as pilocarpine, eserine salicylate, carbachol, and demecarium bromide; mydriatics such as atropine sulfate, scopolamine, tropicamide and hydroxyamphetamine; sympathomimetics such as epinephrine; beta-blockers, such as betaxolol, levobunolol, metipranolol, adaprolol, alprenoxime, carteolol, and timolol; and other drugs such as acetazolamide, apraclonidine, methazolamide, PGF$_2$-alpha-IE, PGA$_2$-IE, Sulprostone (a prostaglandin), and verapamil.

An advantage obtained by the present invention is that it provides a reliable system for extended delivery of drugs to the tear film and other mucosal surfaces in a convenient drop form as a suspension of microspheres. There is no blurring of the vision as in the case of ointments or gels, and it is comfortable to the eye compared to an ocular insert.

The microspheres used according to the present invention have a binding affinity with a charged drug such that the microspheres will actively take up the drug. The binding affinity of a particular macromolecule for a drug can be determined as follows. The amount of bound drug and free drug are determined.

Bound drug=total amount of drug found in microspheres which is contacted with a solution of the drug and allowed to equilibrate minus volume of solution absorbed by the polymer sample times the concentration of drug in the remaining unabsorbed solution Then, Binding affinity = [Bound drug]/[Free drug] =

$$\frac{[\text{Bound drug}]}{[\text{Total drug}] - [\text{Bound drug}]}$$

Generally, a higher binding affinity provides a longer sustained release of the drug. Preferred microspheres have binding affinities over 0.8, and preferably 1.0 and higher. Particularly useful binding affinities are in the range of 1.0 to 30.0.

The macromolecules of which the microspheres are formed will typically have ionic side chains such as carboxylate or ammonium groups which can bind by ion pairing to ionic groups in the drug. Therefore, the drug to be used in accordance with the present invention is preferably prepared in an ionic form, which can be accomplished in general by formulation conditions which allow for formation of ionic species for drug binding. For example, the drug may be precipitated as a hydrochloride salt, if an amine is present in the drug. If the drug contains acid groups, it may be prepared as a sodium, lithium, etc., salt of the acid. Neutral side chains which can form ion pairs with neutral groups on the drug are also useful. For instance, an amino group and a neutral carboxyl group can self-neutralize to the ammonium cation and the carboxylate anion.

A typical microsphere formulation containing 15% by weight microspheres will bind about 50–75% of the total drug in the original solution with which they are contacted for loading. The loading may be accomplished by contacting the microspheres with a solution containing the drug, and the drug will be actively taken up by the microspheres due to the binding affinity of the macromolecules within the microspheres for the drug. The bound drug will thus be a counterion to an ionic species of the macromolecule.

The microspheres will also contain macromolecules which are cross-linkable. These macromolecules may be the same or different from the macromolecules which have a binding affinity for the targeted drug. Typically, the cross-linkable macromolecule will contain cross-linkable groups such as carboxyl groups, amino groups and/or hydroxyl groups. However, other acidic and basic functions which are cross-linkable may be present and utilized, such as sulfhydryl groups.

The macromolecules which will be cross-linked in the microspheres include, but are not limited to water-soluble or water-swellable polymers such as, polyacrylic acid, polyethylene glycol, polygalacturonic acid, hydroxyethylcellulose, hydroxypropylcellulose, collagen, gelatin, carboxymethylcellulose, pectin, dextran, algin, ethyl cellulose, glycosaminoglycan, chitin, chitosan, and other polysaccharides.

Preferably the microspheres will comprise two or more different types of water-soluble or water-dispersable polymers that are cross-linked to form particles with the preferred diameters wherein at least one of the polymers will be a polymer having sufficient binding affinity with the drug. A single type of cross-linkable macromolecule may also be used, in which case it must also be polyionic.

A preferred embodiment of the microsphere composition is a one-to-one mixture of a soluble protein and a polyionic macromolecule, such as a mixture of collagen and polyacrylic acid.

The hardness of the microsphere can be controlled by the extent of cross-linking and by the type and ratio of polymers present. In general, the more water per volume retained in the microsphere, the softer the microsphere.

The cross-linking agents include carbodiimides, preferably, ethyldimethyl aminopropyl carbodiimide; diisopropyl carbodiimide, or dicyclohexyl carbodiimide. Aldehyde cross-linking agents, particularly formaldehyde, may be used but are not preferred because the aldehyde condensation reaction is reversible and thus can produce reverse reaction products which irritate or be toxic in the eye.

Due to the particle size and softness as hydrogels, the microspheres according to the present invention will not be irritating to the eye, and are unlikely to be removed as foreign particles from the eye by being swept with the tear fluid. Although the microspheres according to the present invention are muco-adhesive, they can be swept from the eye along with the mucin. Since there is a turnover of tears approximately every seven minutes, but mucin turns over approximately every 24 hours, it is believed that the microspheres will remain in contact with tear fluid for at least as long as it takes for the drug to be released.

Hydrogel microspheres, suspended in an appropriate vehicle and instilled in the eye, may be retained for many hours. For example, five hours after instillation, sufficient quantities of the hydrogel microspheres will be present such that they can be swabbed out of the eye. By microscopic analysis of these microspheres, it may be seen that the particles are entangled in, and thus are being retained by, ocular mucin.

Even if left in the eye for an extended period of time, the microspheres need not be bio-erodible. Since bio-erosion is not a significant mechanism of release of the drug from the microspheres according to the invention, bio-erodibility of the microspheres over an extended period of time is not a necessary feature. It is contemplated that the microspheres will be removed from the eye with normal mucin turnover, and that the drug will be released from the microspheres prior to any substantial degradation of the microspheres by the enzymes in the eye.

Several methods are known for the formation of protein-containing microparticles, however, the present invention also provides an improvement over such methods. The most common of the known methods involves the thermal denaturation or chemical crosslinking of a protein in a water-in-oil emulsion, whereby a solution of a protein is dispersed into an oil phase with the aid of an emulsifier. Since the resulting particles must be rendered water insoluble, a common procedure for this is to add a crosslinking agent directly to the emulsion. The particles may then be purified by washing and isolated. The drug is typically added to the initial protein solution to be incorporated into the microspheres.

There are several difficulties in the application of the above method to the fabrication of collagen-containing microspheres. First, a protein (not collagen) solution of 25 to 50% is commonly used, but it is not possible to obtain collagen solutions of this concentration. An effective upper concentration limit for collagen solutions is 4 to 5%. Thus, direct application of the above described procedure will give collagen microspheres with very high water content. Moreover, collagen solutions are typically very viscous and "sticky". As a result, a high degree of aggregation occurs when the above conditions are used to fabricate collagen microspheres.

Therefore, an improved and preferred method is provided to fabricate collagen microspheres. First, a water-in-oil emulsion is formed. Using a hydrophobic emulsifier (such as, Span 80) the solution of collagen is emulsified in an organic solvent. If this emulsion is treated with a cross-linking agent, after several minutes the microparticles usually begin to coalesce. Typically after about 30 min the collagen would have completely precipitated from solution as a single mass. According to the improved method, instead of crosslinking the collagen in the emulsion, the emulsion is added to several volumes of a water miscible solvent before the crosslinking reaction is carried out. Apparently, the water miscible solvent dehydrates the emulsion particles, and by some manner this reduces the adhesive properties during the crosslinking step.

The microparticles may also be directly formed using known spray drying technology. For example, an aerosol of a dilute solution of macromolecules can be introduced into a stream of hot air, whereby the water is quickly evaporated. The dried particles are collected using, for example, a cyclone separator. The dried particles are cross-linked by dispersing into a water miscible solvent and adding to this dispersion a crosslinking agent.

A preferred class of macromolecules which will comprise the microspheres comprises a mixture of a first macromolecule containing carboxylic acid functional groups, and a second macromolecule containing amino or hydroxyl functional groups wherein the ratio in the mixture of the first macromolecule to the second macromolecule is in a range of 25:75 to 75:25. According to one method of preparing the microspheres an aqueous solution with an appropriate surfactant such as a fatty alcohol, an ether, or polymer is mixed in a volume ratio in the range of 10:1 to 5:1 and dispersed. Typical surfactants include Pluronics®, Spans® and Tweens® of H.L.B. (hydrophilic-lipophilic balance) value of 1 to 25, glycol monolaurate, polyoxy-ethylene sorbitan monooleate, and the like. The ratio of surfactant to macromolecules is not particularly critical to obtaining suitable microspheres although efficiency of utilization of the macromolecule starting materials may be maximized by selecting optimal macromolecule to surfactant ratios. Typical surfactant amounts are about 4 to 40% by weight. The resulting dispersion is mixed in a water-immiscible organic solvent, such as benzene or toluene, wherein the volume ratio of the aqueous dispersion to the organic solvent is about 1:1 to about 1:5, which thus forms an emulsion. At this point microspheres are formed, but they are relatively unstable and contain a substantial amount of water. Therefore an improvement according to the present invention in forming hydrogel microspheres is to thereafter combine the emulsion with a sufficient volume of water-soluble organic solvent, preferably three to eight volumes, and then adding the cross-linking agent to cross-link the resulting microspheres. A suitable water-soluble organic solvent is acetone, but others may be used provided that they do not interfere or react with the cross-linking agent. This dilution in the water-soluble organic solvent is important in that the excess water is leached out of the microspheres thereby stabilizing them as well as preparing them for cross-linking.

Another method for preparing the microspheres is to form an aqueous solution of a mixture of a macromolecule containing a carboxylic functional group and a macromolecule containing an amino or hydroxyl functional group wherein the mixture of the first macromolecule to the second macromolecule is in a range of about 25:75 to 75:25. Dry particles may then be formed by spray drying this solution. The spray-dried particles are then collected and diluted with a water-soluble organic solvent, and a cross-linking agent is added as described above.

Due in part to the active binding of the drug to the macromolecules in the microspheres, the drug can be loaded into the microspheres after the microspheres have been formed, therefore the microspheres can be sterilized in the absence the drug. Furthermore, the active binding allows the microspheres to take up a substantial portion of the drug loading solution. Due to the active binding, the concentration of the drug within the microsphere is larger than the concentration of the drug in the surrounding vehicle, which is an improvement over prior art methods whereby the microspheres act as sponges and only absorb the drug to a concentration which is the same as the concentration in the loading solution to which the microspheres are exposed.

According to the present invention, it is preferred that the concentration of the drug within the microsphere be at least 200% of the concentration of the drug in the surrounding formulation (vehicle). Thus in a 10% volume of microspheres in a vehicle, 10% bound drug in the microspheres will result in doubling of the drug concentration within the microspheres resulting in material with a binding affinity of 1.0. Furthermore, in prior art methods which require that the drug be loaded into the microsphere during fabrication of the microsphere, in order to sterilize the microsphere, both the drug and the microsphere must be exposed to the sterilizing conditions which can be harsh, leading to degradation of the drug and production of side products which must be proven to be safe. According to the present invention sterilization may be carried out prior to drug loading, thus loading can be accomplished by combining sterile microspheres with a sterile solution of the drug.

While not intending to be bound by any theory, when the drug-loaded microspheres are placed in the eye, the release of bound drug is initiated by ion exchange with the ionic species naturally present in the tear. The drug in the microspheres is also released by diffusion out of the microspheres. Due to the affinity of drug for the microspheres, and due to the diffusion limitation to transport in the microspheres, drug release is prolonged, thus providing drug for a longer period in the eye than that achievable by a single application of an eyedrop solution.

The following examples are provided by way of illustration and are not intended to limit the invention in any way.

EXAMPLE I

Preparation of Hydrogel Microspheres

Two grams of collagen were dissolved into 100 ml of distilled water with gentle agitation. After the collage had completely dissolved the pH of the solution was adjusted to 6.0 with a solution of sodium hydroxide or hydrochloric acid. Two grams of poly-acrylic acid (Carbopol 934P, Goodyear) were dissolved into 100 ml of distilled water with gentle agitation. After the polyacrylic acid had completely dissolved, the pH of the solution was adjusted to 6.0 with a solution of sodium hydroxide or hydrochloric acid.

Five grams of the collagen solution were combined with 5 grams of acrylate solution and diluted with 10 ml of distilled water. To this solution, 4 grams of sorbitan monooleate was added and the resulting mixture was thoroughly mixed. Using a high shear mixer, 25 ml of toluene was slowly added and an emulsion was formed. The resulting emulsion was poured into 8 volumes of acetone with gentle mixing. A dispersion of microspheres was formed. A solution of 15 mg of ethyldimethylaminopropyl carbodiimide in 1 ml of water and 10 ml of acetone was added to the dispersion. The mixture was allowed to react for 1 hour.

The microspheres were isolated by centrifugation. The isolated microspheres were resuspended into 30 ml of acetone and isolated by centrifugation. This procedure was repeated 2 more times. The acetone washed microspheres were suspended in 40 ml of 5 mM acetate buffer (pH=5) and then isolated by centrifugation. The procedure was repeated 2 times substituting distilled water for acetate buffer. Two ml of water were added to the isolated microsphere to yield a concentrated slurry of microspheres.

The concentrated slurry may be sealed in a vial and sterilized by exposure to ionizing radiation.

EXAMPLE II

Drug Loading of Hydrogel Microspheres

Three hundred thirty ul of concentrated slurry, prepared as described in Example I, was added to 670 ul of a 3% drug solution. The solution was gently mixed for 5 min. The resulting solution contains drug loaded microspheres. The slurry was initially translucent but quickly became white and opaque upon addition of the drug solution. The amount of the drug incorporated into the microspheres was determined by measuring the concentration of drug in the aqueous portion of the microsphere dispersion and comparing that to the amount of drug added to the solution, the difference being the amount incorporated into the microsphere.

EXAMPLE III

An In Vitro Tear Film Model

A 500 ul reservoir with 2 openings on opposite sides was filled with a 1% aqueous solution of drug. The reservoir contained a 0.45 um filter between the two openings. The inlet was connected to a peristaltic pump via silicone tubing. The reservoir was perfused with physiological saline solution and the eluate was collected. The rate of perfusion was adjusted such that the rate of elimination of drug from the reservoir was comparable to the rate of elimination of a drug from the tear film of the eye. This rate of perfusion was used for all subsequent experiments. The concentration of drug in the eluate was determined by UV spectroscopy and graphed versus time. The results are presented in the FIGURE. The drug concentration in the eluate was about 0.0005% by about 1¾ hours.

EXAMPLE IV

In Vitro Release of a Drug from Hydrogel Microspheres

A dispersion of drug loaded microspheres, prepared as described in Example II, was placed into a 500 ul reservoir described in Example III. The reservoir was perfused with physiological saline solution and the eluate was collected. The concentration of drug in the eluate was determined by UV spectroscopy and graphed versus time. The results are presented in the FIGURE. The drug concentration in the eluate was about 0.01% at five hours.

EXAMPLE V

Test of Bioerosion of Collagen/Acrylate Microspheres

Cross-linked collagen/polyacrylate composite microspheres were prepared to determine how long they will reside in the tear film. If the residence time is shorter than the time required to release the drug, a fraction of the drug will not be available for penetration into the eye. Collagen devices such as the corneal shield are known to erode in the tear film, presumably due to the presence of proteolytic enzymes. Since the microspheres prepared in this example are 50% collagen, they could be subject to the same degradative mechanisms as the collagen corneal shields. Collagen/acrylate microspheres are prepared as follows.

A one percent solution of collagen is prepared by dissolving 1 gram of collagen in 100 ml of distilled water with gentle agitation. After the collaten has completely dissolved, the pH of the solution is adjusted to 6.0 with a solution of sodium hydroxide or hydrochloric acid. One gram of polyacrylic acid (Carbopol 934 P. Goodyear) is dissolved into 100 ml of distilled water with gentle agitation. After the poly-acrylic acid has completely dissolved the pH of the solution is adjusted to 6.0 with a solution of sodium hydroxide or hydrochloric acid.

Forty grams of the collagen solution is combined with 40 grams of acrylate solution. To this solution, 16 grams of sorbitan monocleate is added and the resulting mixture is thoroughly mixed. Using a high shear mixer, 100 ml of toluene is added slowly and an emulsion is formed. The resulting emulsion is poured into 1.41 of acetone with gentle mixing. A dispersion of microspheres is formed. A solution of 75 mg of ethyldimethylaminopropyl carbodiimide in 2 ml of water and 10 ml of acetone is added to the dispersion. The mixture is allowed to react for 2 hours.

The microspheres are isolated by centrifugation. The isolated microspheres are resuspended in 40 ml of acetone and isolated by centrifugation. This procedure is repeated 2 more times. The acetone washed microspheres are suspended in 40 ml of 5 mM acetate buffer (pH=5) and then isolated by centrifugation. The procedure is repeated 2 time substituting distilled water for acetate buffer. Two ml of water are added to the isolated microsphere to yield a concentrated slurry of microspheres. The concentration and the swell value of the microspheres are then measured.

Approximately 1 ml of microsphere suspension is placed in a tared 2 ml centrifuge vial and weighed. The microspheres are centrifuged at about 15K G's for 3 to 4 min. The excess water is decanted and the compacted microspheres are again weighed. The concentration of microspheres in the slurry is defined to be 0.67×wt of compacted microspheres÷wt of initial slurry. The compacted microspheres are quantitatively transferred to a tared aluminum pan and dried in an oven at 150° C. The swell of the microspheres is defined as 0.67×wt of compacted microspheres÷wt of the dried microspheres. Typical swell values lie between 11 and 17.

Eight tared 2 ml centrifuge tubes were charged with approximately 250 mg of collagen/acrylate microspheres. The weight of the microspheres was determined. One ml of PBS (phosphate-buffered-saline) was added to 4 of the tubes and one ml of a collagenase-PBS solution (0.1 units collagenase/ml) was added to the other four tubes. The suspensions were incubated at 37° C. At the end of 90 min the microsphere suspensions were centrifuged and the wt of the microspheres was recorded. Fresh solutions were added to the tubes and the incubation continued for another 22 hrs. The weight was then again determined and fresh solutions were once again added. The suspensions were further incubated at 37° C. and the weight of remaining microspheres was determined after 88 hrs. The weight lost at each time point corresponds to the weight lost for the microspheres due to erosion.

Serving as positive controls, collagen corneal shields that are designed to dissolve in the tear film in 12 hours were also incubated in the PBS and PBS/collagenase solution. Microspheres having a swell value of 17±0.74 were used to bias the experiment towards faster erosion since the rate of erosion will be fastest for lightly crosslinked microspheres. Weight percentages lost or gained from the incubated microspheres are summarized in the table below in Table 1.

TABLE 1

Weight Percent Gain or Loss From Microspheres

|  | PBS + 0.1 u/ml collagenase | PBS |
| --- | --- | --- |
| 90 minutes | −4.1 ± 2.7 | −7.8 ± 7.3 |
| 22 hours | +1.9 ± 2.6 | −8.1 ± 2.5 |
| 88 hours | +1.6 ± 1.35 | −8.4 ± 3.6 |

A small decrease in the weight of the microspheres was observed initially in both the PBS and the collagenase solutions, most likely due to a change in swell at the beginning of the experiment. The microspheres were initially in a low ionic strength solution, then incubated in the higher ionic strength PBS. It is well documented that the swell of a hydrogel will decrease with increasing osmotic pressure. At subsequent time points there is no further change in the weight of the microspheres in PBS. If degradation were occurring one would observe further weight loss at subsequent time points.

While the microspheres do not degrade in the absence of collagenase, the presence of collagenase does appear to have a minimal effect. There is a small increase in the weight of the microspheres at 22 hours. This can most likely be attributed to the collagenase hydrolyzing a small amount of collagen, thus slightly decreasing the crosslink density of the hydrogel. A decrease in the crosslink density will increase the swell and therefore the weight of the microspheres. However, there is no change between the 22 hour and 88 hour time point (even though a fresh collagenase solution was added after 22 hours) establishing that the microsphere do not erode in the artificial tear film, even after 3½ days.

Collagen corneal shields were incubated in the same solutions that were used for the microspheres. A corneal shield that is designed to dissolve in 12 hours was utilized in this study. The dissolution of the collagen shields was not quantitated but observations were made as to the degree of erosion. Those observations are summarized in the Table 2.

TABLE 2

Corneal Shield Dissolution

|  | PBS + 0.1 u/ml collagenase | PBS |
| --- | --- | --- |
| 90 minutes | Fragments | Intact |
| 22 hours | Completely dissolved | Fragments |
| 88 hours | Completely dissolved | Completely dissolved |

After only 90 minutes, only fragments remained of the collagen shield in the solution containing collagenase. Clinically, a fragmented shield is considered to be fully eroded since it can no longer serve its contact lens function and the fragments will most likely be expelled from the eye. Since those shields are designed to dissolve in the eye after 12 hours, this result confirms that the artificial tear solution is an aggressive model of the ocular environment. The fragments of the collagen shield in collagenase were completely dissolved at the 22 hour time-point, and in 88 hours with the PBS solution.

The data show that there is no measurable erosion of the microspheres in artificial tear solution. The artificial tear solution comprising PBS and 0.1 unit/ml of collagenase functionally dissolves a 12 hour collagen corneal shield within 90 minutes indicating it is an acceptable, if not aggressive model of the ocular environment. This result indicates that there will be essentially no loss of microsphere mass during the expected time of drug release. Since the microspheres do not appear to erode at all (at least for many days), they will be eliminated from the tear film in the eye along with the normal turnover of mucin.

What is claimed is:

1. A method of sustained delivery of a drug to the eye comprising the step of applying to the eye a sustained-release drug delivery composition comprising:

an aqueous carrier containing a pharmaceutically active agent with a pH and osmotic pressure acceptable to the eye;

and cross-linked hydrogel microspheres containing said pharmaceutically active agent, wherein said microspheres have a binding affinity of at least above 0.8 for said agent; wherein said cross-linked hydrogel is cross-linked with an agent selected from the group consisting of ethyldimethyl aminopropyl carbodiimide, diisopropyl carbodiimide and dicyclohexyl carbodiimide.

2. A method according to claim 1 wherein said microspheres comprise cross-linked macromolecules with ionic side chains.

3. A method according to claim 1 wherein said microspheres comprise macromolecules containing ionic side chains and cross-linked macromolecules.

4. A method of sustained delivery of a drug to the eye according to claim 1 wherein composition is mucoadhesive.

5. A method of sustained delivery of a drug to the eye according to claim 1 wherein said cross-linked macromolecules are cross-linked via carboxyl, amino, hydroxyl and/or sulfhydryl groups.

6. A method of sustained delivery of a drug to the eye according to claim 1 wherein said microspheres comprise macromolecules with ionic side chains selected from the groups consisting of carboxylate and ammonium groups.

7. A method of sustained delivery of a drug to the eye according to claim 1 wherein said microspheres comprise collagen.

8. A method of sustained delivery of a drug to the eye according to claim 1 wherein said microspheres comprise polyacrylic acid.

* * * * *